US005662867A

United States Patent [19]
Pugia et al.

[11] Patent Number: 5,662,867
[45] Date of Patent: Sep. 2, 1997

[54] SYSTEM FOR CREATININE DETERMINATION

[75] Inventors: Michael J. Pugia, Granger, Ind.; Michael Salvati, St. Paul, Minn.; Christos Galiatsatos, Athens, Greece

[73] Assignee: Bayer Corporation, Elkhart, Ind.

[21] Appl. No.: 803,851

[22] Filed: Dec. 9, 1991

[51] Int. Cl.$^6$ ................................................. G01N 21/00
[52] U.S. Cl. ........................ 422/56; 436/98; 436/106; 436/111; 436/169
[58] Field of Search ........................ 436/106, 98, 111, 436/166, 169; 422/55, 56, 57; 435/28, 805; 530/209, 201

[56] References Cited

U.S. PATENT DOCUMENTS

| | | | |
|---|---|---|---|
| 3,288,770 | 11/1966 | Butler | 526/204 |
| 4,132,528 | 1/1979 | Eikenberry et al. | 436/169 X |
| 4,543,325 | 9/1985 | Albert et al. | 436/512 X |
| 4,774,192 | 9/1988 | Terminiello et al. | 422/56 X |
| 4,812,399 | 3/1989 | Mauck et al. | 422/55 X |
| 4,818,703 | 4/1989 | Pizzolante | 436/106 X |
| 4,950,611 | 8/1990 | Seaton | 436/98 |
| 5,047,329 | 9/1991 | Suzuki | 422/56 X |

FOREIGN PATENT DOCUMENTS

| | | |
|---|---|---|
| 1128164 | 5/1989 | Japan. |
| 8810429 | 12/1988 | WIPO. |

OTHER PUBLICATIONS

22 Kirk–Othermer Encyclopedia of Chemical Technology, 332–292 (3d ed., New York, John Wiley & Sons, 1983).
"7545. Polyethylene Glycol." *The Merck Index*, 1204 (11th ed., Rahway, NJ, Merck & Co., Inc. 1989).
Patent Abstracts of Japan, vol. 13, No. 375 (p. 921) 21 Aug. 1989.
JP–A–11 29 164 (Eiken Kagaku K.K.) 22 May 1989.
Benedict and Behre, *J. Biol. Chem.*, 114:515–532 (1936) "Some Applications of A New Color Reaction for Creatinine".

*Primary Examiner*—Jill Warden
*Assistant Examiner*—Maureen M. Wallenhorst
*Attorney, Agent, or Firm*—Jerome L. Jeffers

[57] ABSTRACT

Disclosed is a dry reagent system involving an absorbent carrier incorporated with a dye precursor which undergoes a detectable response in the presence of creatinine under strongly basic conditions and which also contains a moderating agent for the strong base which is a polyglycol or a polymerized quaternary ammonium salt.

2 Claims, No Drawings

SYSTEM FOR CREATININE DETERMINATION

BACKGROUND OF THE INVENTION

Creatinine is the end metabolite when creatine becomes creatine phosphate and is used as an energy source for muscle contraction. The creatinine produced is filtered by the kidney glomeruli and then excreted into the urine without reabsorption. The determination of creatinine in body fluids is useful for diagnosing muscle diseases or various kidney diseases such as nephritis and renal insufficiency.

The first practical test for the determination of creatinine in urine, known as the Jaffe method, involves the formation of the red-yellowish brown colored creatinine picrate by the bonding of picric acid and creatinine in an alkaline solution. A more recent method for creatinine determination is reported by Benedict and Behre *J. Biol. Chem.*, 113:515 (1936) which involves the reaction of 3,5-dinitrobenzoic acid with creatinine in an alkaline medium.

Each of these reactions require a high pH, i.e. on the order of 12–13, in order to deprotonate the creatinine so that the system can operate properly. Strongly basic substances such as alkali and alkaline earth metal hydroxides are typically used to maintain a suitably high pH in these reagent systems. This, however, presents several problems when an absorbent carrier such as filter paper or a porous film is used as carrier for the reagent system because upon introduction of the alkali, the carrier tends to become brittle and it is difficult to obtain even distribution of the alkali throughout the carrier matrix. Furthermore, when the reagents are applied to the carrier in the form of a solution whereupon the solvent is evaporated to leave a dry residue, the dried alkali does not readily solubilize when contacted with a fluid such as urine which is being examined for creatinine concentration.

In Japanese Patent Application No. 62-287261 there is disclosed a method for facilitating the application of alkaline ingredients to absorbent carriers which involves dipping the carrier into an aqueous solution of the alkali and an alkali soluble carboxylic acid derivative polymer followed by application from an organic solvent of a dye precursor which develops color upon reacting with creatinine under alkaline conditions.

SUMMARY OF THE INVENTION

The present invention involves a dry reagent system comprising an absorbent carrier which has dispersed therein a material which is reactive with creatinine under alkaline conditions to provide a detectable response, a base and a moderating agent in proximate contact with the base which moderating agent is:

(a) a polyethylene glycol, polypropylene glycol or copolymers thereof having a molecular weight of greater than about 400; or (b) a polymerized quaternary salt of di or mono allyl, di or tri alkyl ammonium characterized by the formula:

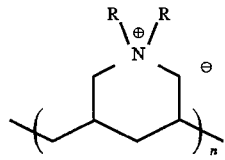

or

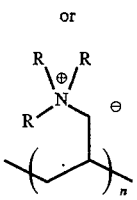

or a copolymer thereof wherein R is straight or branched chain alkyl of 1 to 4 carbon atoms, n is a number of at least 9 and θ represents a counteranion.

DESCRIPTION OF THE INVENTION

The present invention provides a means to moderate the adverse effects of alkali on an absorbent carrier used for the semi-quantitative detection of creatinine in aqueous fluids, particularly in urine. Suitable carrier materials are known in the art and include absorbent papers, woven and nonwoven cloth, glass fiber filters as well as polymeric membranes and films.

The absorbent carrier, which is typically cut into the form of a test strip, is impregnated with a substance which, under alkaline conditions, will react with creatinine to provide a detectable response, such as the formation of a colored reaction product. Suitable materials include picric acid, 3,5-dinitrobenzoic acid, 3,4-dinitrobenzoic acid, 2,4-dinitrobenzene sulfonic acid, (3,5-dinitrobenz)yl alcohol, (3,5-dinitrobenzo)-nitrile, (3,5-dinitrobenz)amide and N,N-diethyl-(3,5-dinitrobenz)amide. In addition there is included in the test strip a base and a moderating agent therefor. While the particular base used is not critical, it must be a strong base and be present in sufficient concentration to raise the pH to a range of about 12–13 in the reaction zone of the reagent system in order for the creatinine to readily react with the creatinine reactive dye precursor to provide the detectable response. Such bases include the alkali and alkaline earth metal hydroxides such as sodium, potassium, lithium, calcium and magnesium hydroxide. It is apparent that this concentration of alkaline material can have a serious detrimental effect on the absorbent carrier material. It has been discovered, however, that certain polymeric materials can be added to the reagent system to moderate the effect of the base thereby providing reagent strips which are more sensitive in producing the detectable response and provide this response in a more consistent manner.

The creatinine determination test system of this invention accomplishes the determination of creatinine by reading the degree of color development of the dye precursor contained therein as a measure of its reflectance and comparing this with a previously-prepared calibration curve. One can also perform a semi-quantitative determination by comparing the degree of color development in the test system visually with a previously prepared color chart.

While we do not wish to be bound by any particular theory of the mechanism of how the invention operates, it is believed that the polymeric moderating agent complexes the hydroxide anion. This complexation prevents association of the hydroxide with the carrier thereby preventing its degradation. This is particularly important when the carrier is derived from paper since the hydroxide is quite deleterious to cellulose. It is hypothesized that the hydroxide anion, when complexed by the moderating polymer of the present invention is more evenly coated onto the carrier since it is in association with the complexing polymer and the polymer/ hydroxide complex is evenly deposited on the fibers of the absorbent carrier. Since the polymers useful in the present invention are water soluble, the hydroxide ion associated with the polymer is more readily solubilized upon rehydration because the hydroxide is not imbedded in the fibers of the carrier.

Suitable moderating agents include polyethylene and polypropylene glycols provided they have a molecular weight of greater than about 400. Lower molecular weight polyglycols are not suitable since they have a much weaker association with the hydroxide anion and its metallic cation. At least 9 oxygens are required for association strong enough to desolvate the metal hydroxide. The upper limit of molecular weight is not critical although from a practical point of view the upper limit on the molecular weight is approximately 750,000. A molecular weight range of from greater than about 400 to about 10,000 is preferred.

The polyglycols can be capped since it is not necessary that they contain terminal hydroxyl groups in order to function in the context of the present invention. Typical end caps include alkyl groups such as methyl to distearate or aryl groups such as 4-nonyl benzenes which are available from specialty chemical manufacturers.

It has also been discovered that a class of polymerized quaternary ammonium salts serve to modify the dilaterious effect of the alkali on the carrier material. These polymers are prepared by polymerizing allyl or diallyl quaternary ammonium salts in which the valence bonds of the nitrogen not occupied by an allyl group are occupied by straight or branched chain alkyl groups of 1–4 carbon atoms. These salts and the polymers obtained by their polymerization typically have a halide, e.g. chloride or bromide, as the counteranion but may be represented by other counteranions such as acetate. Poly (diallyl dimethyl ammonium chloride) is the preferred species and can be obtained from Polysciences, Inc. The degree of polymerization for these polymers, i.e. value of n in the above formula, is typically from 9 to about 1,000 with a value of 9 to 300 being preferred. As is the case with the polyglycols, these polymers must be of sufficiently high molecular weight to accomplish complete complexing of the alkali for effective moderation of its deleterious effects.

The three essential components may be applied to the absorbent carrier by dipping a strip of this material into a solution of the component to be applied. Alternative means of application such as spray coating can be used. It is not essential that the reagent composition be applied in separate steps however, since the dye precursor materials are not water soluble, it is normally applied to the carrier in a separate treatment with the moderating polymer and alkali being applied from a separate aqueous solution. While the polymer and alkali can be applied from a single dip solution, it is preferred that the polymer be applied first in order to protect the carrier during the application of the alkali.

Typical dip solutions will contain from 0.1 to 15 weight/volume percent polymeric moderator, whereas the dip solution for the base will run from 0.5 to 2.5 molar (M). Dip solutions of from 10 to 150 millimolar (mM) are suitable for the dye precursor. Solvents for the dip solutions may be aqueous or organic depending on the solute.

The method of practicing the present invention is further illustrated by the following examples:

EXAMPLE I

Test strips, using Whatman 3MM filter paper as the carrier, were prepared by dipping them into 3 separate solutions and, after each dip, drying in separate temperature zones at temperatures of 60°, 70° and 80° C. for 5 minutes each. In each case, the first dip contained the polymeric alkali moderating agent. Control strips containing no complexing agent were prepared in a similar manner. Each component was applied from its solution of the indicated concentration.

|  | Component | Concentration |
|---|---|---|
| Dip 1: | Poly(diallyl dimethyl ammonium chloride) (PDDAC) in water | 0.5 w/w % |
| Dip 2: | Potassium hydroxide in ethanol/water (80:20) | 1.75 M |
| Dip 3: | 3,5-dinitrobenzoic acid in acetonitrile | 61.0 mM |

In another experiment test strips were prepared in a similar manner from the following solutions:

|  | Component | Concentration |
|---|---|---|
| Dip 1: | Polyethylene glycol-1000 (PEG-1000) | 6.0 w/w % |
| Dip 2: | Potassium hydroxide in ethanol/water (80:20) | 0.5 M |
| Dip 3: | 3,5-dinitrobenzoic acid in acetonitrile | 61.0 mM |

Strips made from the four formulations (with and without complexing agent) were tested using a CLINITEK® 200 spectrophotometer to determine the K/S value at 530 nm 25 seconds after dipping the strips into water containing creatinine. The K/S value was determined from the equation:

$$K/S = \frac{(1-R)^2}{2R}$$

to transform the reflectance data to a function (K/S) that is proportional to the chromophore concentration. The K/S value is the ratio of absorption (K) to the scattering coefficient (S) as described by Kortum in Reflectance Spectroscopy, Springerverlag, New York, N.Y., (1969) at page 111. In case 1 the strips with PDDAC and the control without this complexing agent were tested using a creatinine solution at a concentration of 400 mg/dL while case 2, with and without PEG-1000 was carried out using a creatinine solution at a concentration of 300 mg/dL. The percent coefficient of variation (CV) of the K/S value for 5 separate runs represents the strip variability.

TABLE 1

| Formulation | K/S at 530 nm | % CV |
|---|---|---|
| Case 1 without PDDAC | 6.3 | 12.1 |
| Case 1 with PDDAC | 9.9 | 6.0 |
| Case 2 without PEG-1000 | 1.31 | 30.4 |
| Case 2 with PEG-1000 | 1.97 | 21.8 |

From the data of Table 1, it can be determined that formulations containing either moderating agent (PDDAC or PEG-1000) have greater reactivity and lower variability than strips formulated without this agent since the K/S values are higher and the % CV values are lower for the formulations containing the moderating agent.

EXAMPLE II

The experiment of Example I was repeated with the exception that polyethylene glycols having molecular weights of 400 and 1,000 as well as a polypropylene glycol having a molecular weight of 2,000 were used as the moderating agent by dipping the test strips into aqueous solutions of these polymers (6% w/w) and then dipping them into a 0.5M potassium hydroxide solution. In each case 3,5-dinitrobenzoic acid was applied by dipping the strips into its 28 mM ethanol solution. The results of this experiment are summarized in Table 2.

TABLE 2

| Polymer | K/S | % CV |
| --- | --- | --- |
| Control (no polymer) | 1.24 | 34.1 |
| PEG 1000 | 1.89 | 18.5 |
| PEG 400 | 1.16 | 31.2 |
| PPG 2000 | 1.94 | 14.2 |

From Table 2 it can be determined that the low molecular weight PEG 400 had little effect on the test strips since the K/S value and % CV were virtually unchanged vis-a-vis the control. Consequently, one would normally select a glycol having a molecular weight greater than 400 for use in the present invention. Conversely, those test strips treated with PEG 1000 and PPG 2000 exhibited greater absorption as indicated by the K/S values and significantly less variation as indicated by the reduced coefficient of variation.

What is claimed is:

1. In a dry reagent system comprising paper as an absorbent matrix which has dispersed therein 3,5-dinitrobenzoic acid as a dye precursor which is reactive with creatinine under alkaline conditions to provide a colormetric response together with an alkali or alkaline earth metal hydroxide in sufficient concentration to maintain the pH of the system at a level of from about 12–13 upon rehydration of the dried reagent system, the improvement which comprises the presence of poly(diallyl dimethyl ammonium chloride) having a degree of polymerization of at least 9 as a moderating agent for the hydroxide, said moderating agent being substantially uniformly dispersed throughout the paper matrix.

2. A dry regent test device comprising an absorbant carrier incorporated with a test composition comprising a dye precursor which is reactive with creatinine at a pH of from about 12 to 13 to provide a colored response, a base of sufficient strength and concentration to create an alkaline condition necessary to provide the colored response upon rehydration of the test device and a moderating agent wherein the moderating agent is poly(diallyl dimethyl ammonium chloride) having a degree of polymerization of from 9 to about 1,000.

* * * * *